United States Patent
Cha et al.

(10) Patent No.: US 7,361,149 B2
(45) Date of Patent: Apr. 22, 2008

(54) PRESSURE-DEPENDENT AUTOMATIC LEAK VALVE FOR SPHYGMOMANOMETERS

(76) Inventors: Eun Jong Cha, Jukong Apt. 208-205, Mochung-Dong, Heungdeok-Gu, Cheongui-City, Chungcheonbuk-Do (KR); Kyung Ah Kim, 1207, Dukhee apt., Sajik 2-Dong, Heungdeok-Gu, Cheongju-City, Chungcheongbuk-Do (KR) 361-102; Sung Hoon Kim, Gangyoung Apt. 101-903, 1-19 Gaeshin-Dong, Heungdeok-Gu, Cheongui-City, Chungcheongbuk-Do (KR) 361-240

( * ) Notice: Subject to any disclaimer, the term of this patent is extended or adjusted under 35 U.S.C. 154(b) by 0 days.

(21) Appl. No.: 11/267,168

(22) Filed: Nov. 7, 2005

(65) Prior Publication Data

US 2006/0264765 A1 Nov. 23, 2006

(30) Foreign Application Priority Data

May 23, 2005 (KR) ...................... 10-2005-0042817

(51) Int. Cl.
*A61B 5/02* (2006.01)
*F16K 25/00* (2006.01)

(52) U.S. Cl. ...................... 600/498; 251/175; 251/176
(58) Field of Classification Search ........ 600/490–499; 137/565.13; 251/157, 175, 176, 336, 337
See application file for complete search history.

(56) References Cited

U.S. PATENT DOCUMENTS

| 4,418,699 | A | * | 12/1983 | Chen | .......................... 600/498 |
| 5,323,806 | A | * | 6/1994 | Watari et al. | ................ 137/504 |
| 5,447,160 | A | * | 9/1995 | Kankkunen et al. | ........ 600/490 |
| 7,018,337 | B2 | * | 3/2006 | Hood, Jr. | ..................... 600/490 |

\* cited by examiner

*Primary Examiner*—Charles A. Marmor, II
*Assistant Examiner*—Navin Natnithithadha
(74) *Attorney, Agent, or Firm*—Birch, Stewart, Kolasch & Birch, LLP

(57) ABSTRACT

A pressure-dependent automatic leak valve for sphygmomanometers is able to regularly reduce the pressure in a cuff without manipulation of a pressure reducing valve. Fluid resistance of air to be discharged through the pressure-dependent automatic leak valve is automatically changed so that air is discharged at a constant rate, and the pressure in the cuff is reduced at a constant speed.

3 Claims, 2 Drawing Sheets

PRESSURE-DEPENDENT AUTOMATIC LEAK VALVE FOR SPHYGMOMANOMETERS

CROSS-REFERENCES TO RELATED APPLICATIONS

This application claims priority under 35 U.S.C. § 119(a) on Patent Application No. 10-2005-0042817 filed in Korea on May 23, 2005, the entire contents of which are hereby incorporated by reference.

BACKGROUND OF THE INVENTION

1. Field of the Invention

The present invention relates generally to sphygmomanometers and, more particularly, to a pressure-dependent automatic leak valve for sphygmomanometers which is able to constantly reduce the pressure in a cuff without manipulation of a pressure reducing valve.

2. Description of the Related Art

Generally, intraarterial blood pressure periodically and repeatedly increases and decreases with systole and diastole, that is, according to the heartbeat. The maximum value in a periodic conversion cycle of blood pressure (BP) is called systolic pressure ($P_{SYS}$), and the minimum value is called diastolic pressure ($P_{DIAS}$). Furthermore, typically, blood pressure is expressed in $P_{SYS}/P_{DIAS}$, and its unit is mmHg.

The above-mentioned method of measuring blood pressure is noninvasive. Typically, a pressure obtained by pressing a portion of the arm of a human is expressed in Pc, and blood pressure in arteries in the arm is expressed in BP. Noninvasive blood pressure measurement uses a principle in that, because tissue, which is peripheral to the arteries, transfers compression pressure Pc to the arteries without loss, the arteries are closed or opened according to Pc and Bp.

If the compression pressure Pc is greater than the blood pressure BP, the arteries are closed. In the opposite case, the arteries are open. Therefore, if the Pc is sufficiently large, that is, in the case of Pc>$P_{SYS}$, all arteries are closed. If the Pc which has been applied to the arm, is reduced, the arteries which have been closed, are slowly opened. Then, turbulent blood is forced through the narrowed arteries by the heart. At this time, it is possible to auscultate a sound around there. This sound is called a Korotkoff sound.

After this Korotkoff sound is heard, when the arteries are completely opened by further reducing the Pc, that is, when the state of Pc<$P_{DIAS}$ is reached, the sound disappears.

Here, the value of Pc at the point in time that the Korotkoff sound is heard is determined as a value of $P_{SYS}$, and the value of Pc at the point in time that the Korotkoff sound disappears is determined as a value of $P_{DIAS}$. Noninvasive blood pressure measurement is a method using this principle.

A mercury column sphygmomanometer is a representative example of sphygmomanometers using the principle of noninvasive blood pressure measurement. Typically, the conventional mercury column sphygmomanometer includes a cuff which is wound around the arm of a human to compress the arm using air injected into the cuff, and a mercury column which displays the pressure Pc in the cuff (the pressure is designated by the height of the mercury column and is expressed in mmHg units). The mercury column sphygmomanometer further includes an air injector which has a bulb shape and injects air into the cuff when a user squeezes the air injector with his/her hand, thus increasing the pressure in the cuff. The mercury column sphygmomanometer further includes a pressure reducing valve through which air is discharged. Here, the user can adjust a pressure reduction speed of the pressure reducing valve by rotating a screw type knob of the pressure reducing valve with the hand.

In the mercury column sphygmomanometer having the above-mentioned construction, as shown in FIG. 1, the air injector 10, having a bulb shape, is coupled at a first side thereof to the cuff 20 and communicates at a second side thereof with the atmosphere (A). First and second unidirectional valves 11 and 11' are provided in the air injector 10 at the first and second sides at which the air injector 10 communicates with the cuff 20 and the atmosphere (A), respectively. The pressure reducing valve 30 is disposed around the first unidirectional valve 11 which is located at the side related to the cuff 10. If the user pushes the air injector 10 in an inside direction of the arrow (M) of FIG. 1 while the pressure reducing valve 30 is closed, the second unidirectional valve 11', which is located towards the atmosphere (A), is closed and the first unidirectional valve 11, which is located towards the cuff 10, is opened by the manual pressure generated in the air injector 10. Thus, air, which has been in the air injector 10, flows in the direction of the arrow of FIG. 1 and is injected into the cuff 20. When the user releases the air injector 10, the air injector 10 is returned to the initial state by its elasticity, that is, the air injector 10 returns in the outward direction of the arrow (M) of FIG. 1. Then, the first unidirectional valve 11 is closed and the second unidirectional valve 11' is opened by negative pressure occurring in the air injector 10. Thus, outside air is drawn into the air injector 10 through the second unidirectional valve 11'. The pressure in the cuff 20 is increased by repeatedly conducting this process.

To reduce the pressure in the cuff 20 for measuring blood pressure, the pressure reducing valve 30 is open, so that air in the cuff 20 is discharged outside. Then, the pressure in the cuff 20 is reduced. At this time, the user is able to regulate the speed of pressure reduction in the cuff 20 using the screw structure of the pressure reducing valve 30. However, this regulation is very sensitive, so that a high level of skill has been required.

The operation of measuring blood pressure using such a mercury column sphygmomanometer will be explained herein below. As shown in FIG. 2, the cuff 20 is wound around an arm. Thereafter, while the pressure reducing valve 30 is completely closed, air is injected into the cuff 20 by the air injector 10 until the pressure Pc in the cuff 20 becomes sufficiently higher than the systolic pressure $P_{SYS}$. Then, the pressure of a mercury column gauge 40 is increased. After air is injected into the cuff 20 such that Pc becomes sufficiently higher than $P_{SYS}$, the pressure reducing valve 30 is slightly opened so as to slowly reduce Pc. Typically, Pc is reduced at a speed ranging from −3 to −5 mmHg/sec. While Pc is gradually reduced, the Korotkoff sound occurs. When the Korotkoff sound is heard, the user immediately reads the height of the mercury column using a stethoscope 50 and determines it as the systolic pressure $P_{SYS}$. Continuously, while the Pc is reduced, the user immediately reads the height of the mercury column at the point of time that the Korotkoff sound disappears, and determines it to be the diastolic pressure $P_{DIAS}$.

However, to measure blood pressure using the conventional mercury column sphygmomanometer, sufficient skill is required. In other words, the user must precisely hear the occurrence and elimination points of the Korotkoff sound with the ears and, simultaneously, must precisely reads the height of the mercury column at those points with the eyes. As well, the user must carefully regulate the pressure reducing valve such that the pressure reduction speed becomes −3 to −5 mmHg/sec.

Meanwhile, if a computer is used, the computer controls a motor of the pressure reducing valve, but, because there is a probability of malfunction of the motor, problems still remain.

SUMMARY OF THE INVENTION

Accordingly, the present invention has been made keeping in mind the above problems occurring in the prior art, and an object of the present invention is to provide a pressure-dependent automatic leak valve for sphygmomanometers which is able to regularly reduce the pressure in a cuff without manual manipulation of a pressure reducing valve or the use of a motor for the pressure reducing valve.

In order to accomplish the above object, the present invention provides a pressure-dependent automatic leak valve, including: an outer casing, with an inlet port formed at a predetermined position in the outer casing so that air is drawn from a cuff into the outer casing, and an outlet port formed at a predetermined position in the outer casing so that the air, drawn through the inlet port, is discharged outside through the outlet port; a movable member having a diameter smaller than an inner diameter of the outer casing and inserted into the outer casing; and a spring supporting the movable member in the outer casing.

The movable member may include a movable shaft which is provided on the movable member and has an outer diameter smaller than an inner diameter of the outlet port.

The outlet port of the outer casing may be defined by a thick part such that the inner diameter of the outlet port is smaller than an inner diameter of a part of the outer casing near the inlet port, and an upper end of the movable shaft of the movable member and a lower end of the thick part overlap each other.

The pressure-dependent automatic leak valve may further include a seat provided at a lower position in the outer casing so that the movable member is seated onto the seat.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Hereinafter, a pressure-dependent automatic leak valve for sphygmomanometers according to a preferred embodiment of the present invention will be described herein below with reference to the attached drawings.

Figure 3:
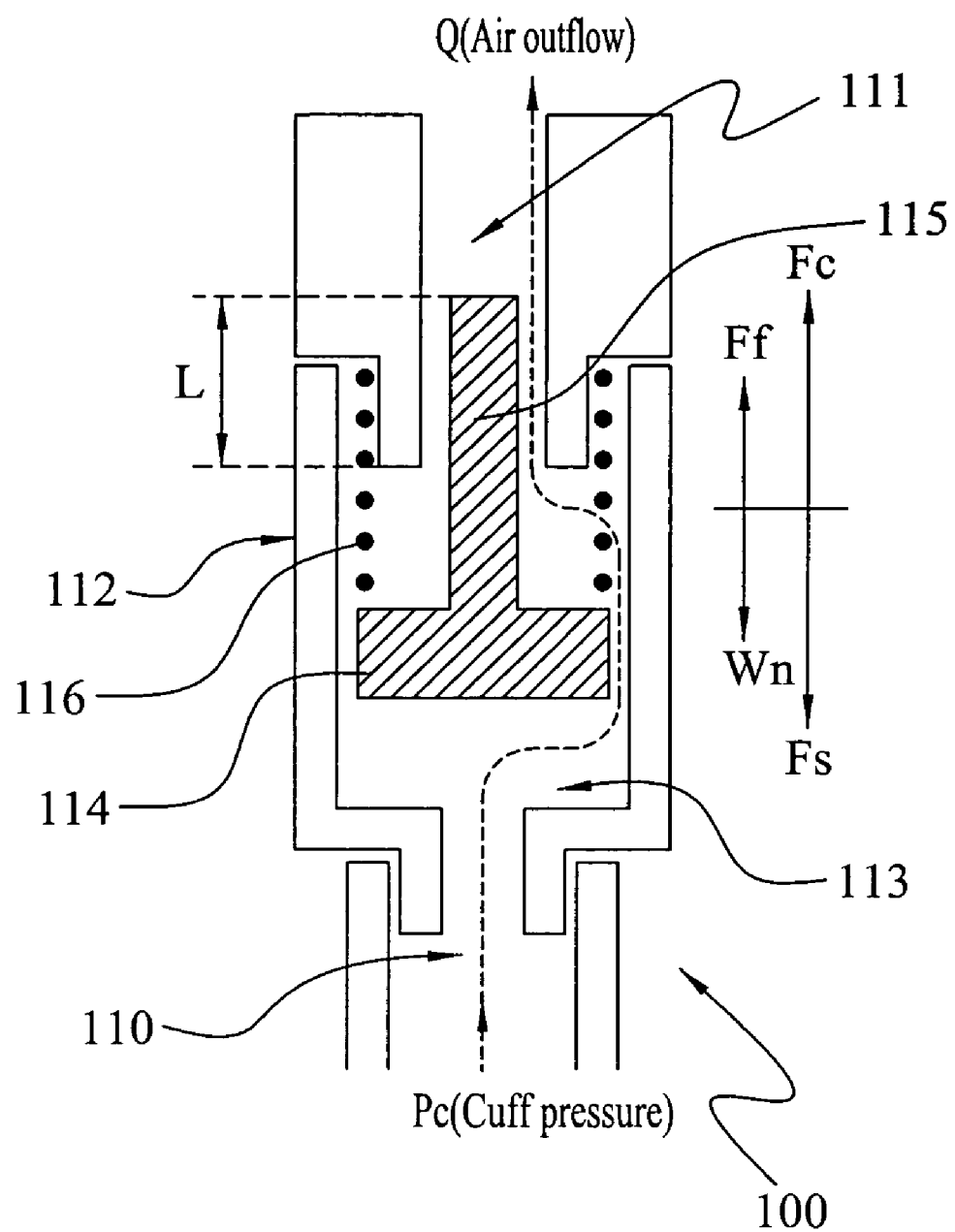
FIG. 3 is a schematic view of a pressure-dependent automatic leak valve for sphygmomanometers, according to a preferred embodiment of the present invention.

FIG. 3 is a schematic view of the pressure-dependent automatic leak valve 100 for sphygmomanometers, according to the preferred embodiment of the present invention.

As shown in FIG. 3, the pressure-dependent automatic leak valve 100 includes an outer casing 112. An inlet port 110 is formed at a predetermined position in the outer casing 112 so that air is drawn from a cuff (not shown) into the outer casing 112. An outlet port 111 is formed at a predetermined position in the outer casing 112 so that the air, drawn through the inlet port 110, is discharged outside through the outlet port 111. The pressure-dependent automatic leak valve 100 further includes a movable member 114 which is seated onto a seat 113, which is provided at a lower position in the outer casing 112. The movable member 114 has a diameter smaller than an inner diameter of the outer casing 112. Furthermore, the movable member 114 includes a movable shaft 115 which extends a predetermined length in a perpendicular direction from the movable member 114 and has a diameter smaller than that of the outlet port 111. The pressure-dependent automatic leak valve 100 further includes a spring 116 which elastically supports the movable member 114 in the outer casing 112.

The pressure-dependent automatic leak valve 100 having the above-mentioned construction is used while held in a vertical orientation, and its usage is as follows.

Figure 1:
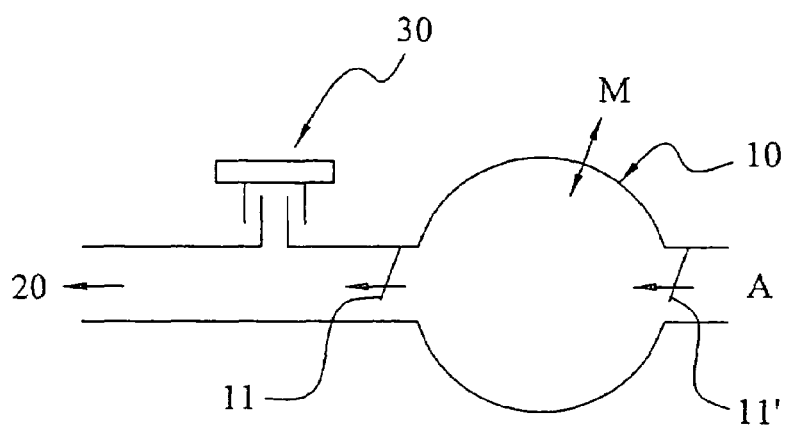
FIG. 1 is a view showing a pressure reducing valve and an air injector of a conventional mercury column sphygmomanometer.
Figure 2:
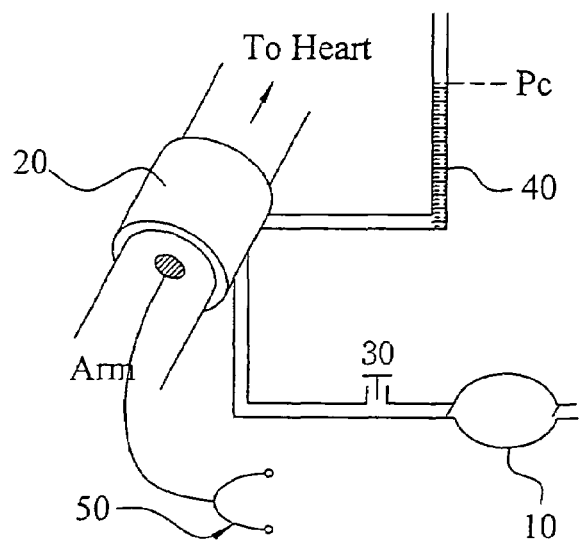
FIG. 2 is a view showing the usage and construction of the mercury column sphygmomanometer of FIG. 1.

As shown in the description of the prior arts, air is injected into the cuff (see, FIG. 2) by an air injector (10 of FIG. 2). However, in the present invention, the pressure-dependent automatic leak valve 100 is used, unlike the conventional art having a pressure reducing valve 30. Because the automatic leak valve 100 is manufactured such that a pressure reduction speed ranges −3 to −5 mmHg/sec, the amount of air discharged through the automatic leak valve 100 during an air injection process is negligible compared to the amount of air injected from the air injector 10 into the cuff 20. Therefore, air can be injected into the cuff 20 using the air injector 10 without separate manipulation of the automatic leak valve 100 until the pressure Pc in the cuff 20 is sufficiently higher than the systolic pressure $P_{SYS}$, in the same manner as that described for the conventional art.

Thereafter, unlike the conventional art having a disadvantage of adjustment of the pressure reducing valve 30, in the present invention, the user merely reads the heights of the mercury column at occurrence and elimination points of a Korotkoff sound using a stethoscope 50, thus determining a systolic pressure $P_{SYS}$ and a diastolic pressure $P_{DIAS}$. Here, the air, which was injected into the cuff 20, is discharged to the outside through the outlet part 111 of the automatic leak valve 100 along a flow path shown by the dashed arrow of FIG. 3. At this time, because the automatic leak valve 100 is vertically set, a frictional force Ff is offset by the weight $W_N$ of the movable member 114 defined by gravity.

The length L of a portion of the movable shaft 115 of the movable member 114, which overlaps with a lower portion of a thick part of the outer casing 112 which defines the outlet port 111, changes according to the cuff pressure Pc. That is, if the cuff pressure Pc is relatively high, the spring 116 is contracted so that the overlapped length L increases. If the cuff pressure Pc is reduced, because the force of air, which pushes the movable member 114 outwards, is reduced, the movable member 114 moves downwards while the spring is restored to its initial state. Thus, the overlapped length L is shortened.

Here, when the cuff pressure Pc is high, air to be discharged through the outlet port 111 rises at high pressure, but, because fluid resistance increases in proportion to the increased overlapped length L, the air passes through the outlet port 111 under high fluid resistance. As a result, the amount of air to be discharged through the outlet port 111 becomes constant due to the balance between the cuff pressure Pc and the fluid resistance. As the cuff pressure Pc is reduced after some air is discharged, air to be discharged rises at low pressure, but, because the overlapped length L is gradually reduced so that fluid resistance is reduced, the air passes through the outlet port 111 under low fluid resistance. Therefore, the amount of air to be discharged through the outlet port 111 becomes constant. In other words, the spring 114 is contracted or expanded according to the cuff pressure Pc. Thereby, the fluid resistance is automatically changed, so that the amount of air to be discharged is maintained at a constant level. The reason for this is that the fluid resistance is in proportion to the overlapped length L.

Furthermore, the automatic leak valve 100 is used while held in a vertical position, such that frictional force Ff occurring between the movable member 114 and the outer casing 112 is offset by the weight Wn of the movable member 114. If not, a constant amount of air cannot be discharged, due to the frictional force Ff.

As such, after the systolic pressure $P_{SYS}$ and the diastolic pressure $P_{DIAS}$ are determined, the cuff 20 is removed from the arm. Then, the pressure in the cuff 20 is passively reduced. Alternatively, because the air injector 10 is coupled to an air inlet of a connection tube connected to the cuff 20, if the air injector 10 is removed from the air inlet of the connection tube, air is directly discharged from the cuff 20 to the outside through the air inlet of the connection tube.

As described above, when a pressure-dependent automatic leak valve of the present invention is used in a sphygmomanometer, a user can reduce air pressure at a constant speed without the skilled pressure reducing valve adjustment ability that has been required in the conventional art. Therefore, the present invention make it possible for the user to efficiently and easily measure the systolic pressure $P_{SYS}$ and the diastolic pressure $P_{DIAS}$ of a human.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A pressure-dependent automatic leak valve, comprising:

an outer casing, with an inlet port formed at a predetermined position in the outer casing so that air is drawn from a cuff into the outer casing, and an outlet port formed at a predetermined position in the outer casing so that the air, drawn through the inlet port, is discharged outside through the outlet port;

a movable member having a diameter smaller than an inner diameter of the outer casing and inserted into the outer casing;

a spring supporting the movable member in the outer casing; and a seat provided at a lower position in the outer casing so that the movable member is seated onto the seat, wherein the movable member comprises a movable shaft provided on the movable member and having an outer diameter smaller than an inner diameter of the outlet port, and wherein the outlet port of the outer casing is defined by a thick part such that the inner diameter of the outlet port is smaller than an inner diameter of a part of the outer casing near the inlet port, and an upper end of the movable shaft of the movable member and a lower end of the thick part overlap each other;

wherein an overlap amount between the movable shaft and the thick part of the outer casing changes dependent upon a pressure exerted upon the movable member by the air from the cuff;

wherein the movable member includes a bottom member to which the movable shaft is attached, and wherein the pressure-dependent automatic leak valve provides an air flow from the cuff that first passes by the bottom member, then through the spring, and then through a gap between the upper end of the movable shaft and the lower end of the thick part, and to the outlet port;

wherein the spring is a coil spring that surrounds the movable shaft of the movable member; and wherein the bottom member has a diameter smaller than an inner diameter of the casing so that air from the cuff may flow therepast on its way to the outlet port.

2. The pressure-dependent automatic leak valve as set forth in claim 1, wherein a flow rate of the pressure-dependent automatic leak valve is determined by an amount of the movable member overlapping with the thick part of the outer casing.

3. The pressure-dependent automatic leak valve as set forth in claim 1, wherein the spring biases the movable member in a direction to decrease an overlap amount between the movable shaft and the thick part of the outer casing.

* * * * *